United States Patent
Minagawa

(10) Patent No.: US 9,339,845 B2
(45) Date of Patent: *May 17, 2016

(54) SURFACE MODIFICATION METHOD AND SURFACE-MODIFIED ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 201 days.

This patent is subject to a terminal disclaimer.

(21) Appl. No.: 13/775,451

(22) Filed: Feb. 25, 2013

(65) Prior Publication Data

US 2013/0310772 A1 Nov. 21, 2013

(30) Foreign Application Priority Data

May 16, 2012 (JP) ................................. 2012-112563

(51) Int. Cl.
| | | |
|---|---|---|
| *B05D 5/08* | (2006.01) | |
| *A61L 29/14* | (2006.01) | |
| *C08J 3/28* | (2006.01) | |
| *C08C 19/28* | (2006.01) | |
| *C08J 7/18* | (2006.01) | |
| *C08F 279/02* | (2006.01) | |
| *A61L 29/04* | (2006.01) | |

(52) U.S. Cl.
CPC ................. *B05D 5/083* (2013.01); *A61L 29/04* (2013.01); *A61L 29/14* (2013.01); *C08C 19/28* (2013.01); *C08F 279/02* (2013.01); *C08J 7/18* (2013.01); *A61L 2400/18* (2013.01); *C08J 2321/00* (2013.01); *Y10T 428/24355* (2015.01); *Y10T 428/31826* (2015.04)

(58) Field of Classification Search
CPC ........ B05D 5/083; A61L 29/04; A61L 29/14; A61L 2400/18; C08F 279/02; C08C 19/28; C08J 7/18; C08J 232/00; Y10T 428/31826; Y10T 428/24388

See application file for complete search history.

(56) References Cited

U.S. PATENT DOCUMENTS

| | | | |
|---|---|---|---|
| 3,418,066 A | 12/1968 | Caldwell et al. | |
| 5,100,689 A | 3/1992 | Goldberg et al. | |
| 5,340,879 A | 8/1994 | Audenaert et al. | |
| 5,637,460 A | 6/1997 | Swan et al. | |
| 5,885,566 A | 3/1999 | Goldberg | |
| 5,967,714 A * | 10/1999 | Ottersbach et al. | 428/424.2 |
| 6,001,894 A * | 12/1999 | Ottersbach et al. | 522/149 |
| 6,203,856 B1 | 3/2001 | Ottersbach et al. | |
| 6,358,557 B1 | 3/2002 | Wang et al. | |
| 6,808,738 B2 * | 10/2004 | DiTizio et al. | 427/2.24 |
| 7,348,055 B2 * | 3/2008 | Chappa | A61L 27/34 |
| | | | 428/319.3 |
| 8,840,927 B2 | 9/2014 | DiTizio et al. | |
| 2002/0161065 A1 | 10/2002 | DiTizio et al. | |
| 2004/0086568 A1 * | 5/2004 | Ditizio et al. | 424/486 |
| 2004/0106732 A1 | 6/2004 | Tsuji et al. | |
| 2007/0003592 A1 | 1/2007 | Hissink | |
| 2007/0116971 A1 | 5/2007 | Yoshikawa et al. | |
| 2008/0016644 A1 | 1/2008 | Mizote et al. | |
| 2008/0312377 A1 | 12/2008 | Schmidt et al. | |
| 2011/0160357 A1 * | 6/2011 | Gerster et al. | 524/83 |
| 2013/0203883 A1 | 8/2013 | Minagawa | |
| 2013/0274367 A1 | 10/2013 | Minagawa et al. | |
| 2013/0310772 A1 | 11/2013 | Minagawa | |
| 2014/0039084 A1 | 2/2014 | Minagawa | |
| 2014/0128493 A1 | 5/2014 | Minagawa | |
| 2015/0203612 A1 | 7/2015 | Minagawa | |

FOREIGN PATENT DOCUMENTS

| | | |
|---|---|---|
| GB | 1120803 A | 7/1968 |
| GB | 1120804 A | 7/1968 |
| JP | 61-209667 A | 9/1986 |
| JP | 62-87163 A | 4/1987 |
| JP | 63-92658 A | 4/1988 |
| JP | 5-179055 A | 7/1993 |
| JP | 6-25450 A | 2/1994 |
| JP | 8-1793 A | 1/1996 |
| JP | 9-67457 A | 3/1997 |
| JP | 10-251350 A | 9/1998 |

(Continued)

OTHER PUBLICATIONS

International Search Report issued in PCT/JP2013/074219 dated Dec. 3, 2013.
U.S. Office Action dated Jun. 24, 2015, for U.S. Appl. No. 14/118,136.
U.S. Office Action dated Sep. 21, 2015, for U.S. Appl. No. 14/107,746.
Allmér et al., "Surface Modification of Polymers. I. Vapour Phase Photografting with Acrylic Acid," Journal of Polymer Science: Part A: Polymer Chemistry, vol. 26, 1988, pp. 2099-2111.
International Search Report, mailed on Jul. 24, 2012, for International Application No. PCT/JP2012/064030.

(Continued)

*Primary Examiner* — Sanza McClendon
(74) *Attorney, Agent, or Firm* — Birch, Stewart, Kolasch & Birch, LLP

(57) ABSTRACT

The present invention aims to provide a surface modification method for a rubber vulcanizate or a thermoplastic elastomer, which can impart excellent sliding properties and durability against repeated sliding motion and can allow the surface to maintain the sealing properties, without using expensive self-lubricating plastics. The present invention relates to a surface modification method for modifying a rubber vulcanizate or a thermoplastic elastomer as an object to be modified, the method including: Step 1 of allowing a photopolymerization initiator to be adsorbed on a surface of the object to be modified; and Step 2 of radical polymerizing monomers, starting from the adsorbed photopolymerization initiator, by irradiation with UV light at a wavelength of 300 nm to 400 nm to grow polymer chains on the surface of the object to be modified.

26 Claims, 2 Drawing Sheets

(56) References Cited

FOREIGN PATENT DOCUMENTS

| | | |
|---|---|---|
| JP | 10-298320 A | 11/1998 |
| JP | 2001-95621 A | 4/2001 |
| JP | 2002-145971 A | 5/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-213516 A | 8/2005 |
| JP | 2007-119563 A | 5/2007 |
| JP | 2007-145884 A | 6/2007 |
| JP | 2009-30074 A | 2/2009 |
| JP | 2009-138169 A | 6/2009 |
| JP | 2010-23710 A | 2/2010 |
| JP | 2010-142537 A | 7/2010 |
| JP | 2010-142573 A | 7/2010 |
| JP | 2010-150349 A | 7/2010 |
| JP | 2011-189562 A | 9/2011 |
| JP | 2011-241190 A | 12/2011 |
| JP | 2012-162646 A | 8/2012 |
| WO | WO 2007/072613 A1 | 6/2007 |
| WO | WO 2011/038483 A1 | 4/2011 |
| WO | WO 2012/091169 A1 | 7/2012 |

OTHER PUBLICATIONS

U.S. Notice of Allowance, issued Dec. 26, 2014, for U.S. Appl. No. 13/956,974.

U.S. Office Action (Requirement for Restriction/Election), issued May 9, 2014, for U.S. Appl. No. 13/956,974.

U.S. Office Action, issued Aug. 25, 2014, for U.S. Appl. No. 13/956,974.

U.S. Office Action, issued May 8, 2015, for U.S. Appl. No. 13/756,837.

U.S. Office Action, issued Oct. 20, 2014, for U.S. Appl. No. 13/756,837.

* cited by examiner

SURFACE MODIFICATION METHOD AND SURFACE-MODIFIED ELASTIC BODY

TECHNICAL FIELD

The present invention relates to a surface modification method, and surface-modified elastic bodies such as: a catheter and a gasket for syringes, each having at least partially a surface modified by the surface modification method; and a tire having at least partially a groove surface, or a sidewall surface, modified by the surface modification method.

BACKGROUND ART

In great consideration of sealing properties, elastic bodies (e.g. rubber) are used for parts that slide while maintaining their, sealing performance, such as gaskets each of which is integrated with a syringe plunger and forms a seal between the plunger and the barrel. Such elastic bodies, however, have a slight problem with their sliding properties (see Patent Literature 1). Hence, a sliding property improving agent (e.g. silicone oil) is applied to the sliding surface. It is pointed out, however, that silicone oil can have a baleful influence on recently marketed bio-preparations. On the other hand, a gasket to which a sliding property improving agent is not applied is poor in the sliding properties, and thus the plunger cannot be pushed smoothly so that it pulsates upon administration, thereby causing problems such as inaccurate injection amount and pain on patients.

In order to simultaneously satisfy such conflicting requirements, that is, the sealing properties and the sliding properties, one technique is proposed in which a self-lubricating PTFE film is applied (see Patent Literature 2). The film, however, is generally expensive and thus increases the production cost of processed products, limiting its application range. Also, products covered with the PTFE film might not be reliable in the case that the products are used in applications in which sliding or the like motion is repeated and durability is thereby required. Another problem is that since PTFE is vulnerable to radiation, it cannot be sterilized by radiation.

Meanwhile, application to other uses requiring sliding properties in the presence of water may be considered. Specifically, water can be delivered without a loss by reducing the fluid resistance of the inner surface of a pre-filled syringe or the inner surface of a pipe or tube for delivering water, or by making its contact angle with water high or greatly low. Also, drainage of water on wet roads and of snow on snowy roads can be improved by reducing the fluid resistance of the groove surface of tires, or by making its contact angle with water high or greatly low. This results in enhanced grip performance and enhanced hydroplaning properties, leading to better safety. In addition, less sticking of wastes and dusts is expected as a result of reducing the sliding resistance of the sidewall surface of tires or walls of buildings, or as a result of making its or their contact angle with water high.

Further advantageous effects can be expected, such as: less pressure loss when water, an aqueous solution, or the like is delivered through a diaphragm such as a diaphragm pump or a diaphragm valve; easy sliding of skis or a snowboard by enhancing the sliding properties of the sliding surface thereof; better noticeability of a road sign or a signboard by enhancing the sliding properties thereof to allow snow to slide easily; reduction in water resistance or drag and less sticking of bacteria on the outer peripheries of a ship by reducing the sliding resistance of the outer peripheries or by making their contact angle with water high; and swimsuits with reduced water resistance or drag by improving the sliding properties of the thread surface thereof.

CITATION LIST

Patent Literature

Patent Literature 1: JP 2004-298220 A
Patent Literature 2: JP 2010-142537 A

SUMMARY OF INVENTION

Technical Problem

The present invention aims to solve the above problems and provide a surface modification method for a rubber vulcanizate or a thermoplastic elastomer, which can impart excellent sliding properties and durability against repeated sliding motion and can allow the surface to maintain the sealing properties, without using expensive self-lubricating plastics. The present invention also aims to provide surface-modified elastic bodies such as: a catheter and a gasket for syringes, each having at least partially a surface modified by the surface modification method; and a tire having at least partially a groove surface, or a sidewall surface, modified by the surface modification method.

Solution to Problem

The present invention relates to a surface modification method for modifying a rubber vulcanizate or a thermoplastic elastomer as an object to be modified, the method comprising:

Step 1 of allowing a photopolymerization initiator to be adsorbed on a surface of the object to be modified; and Step 2 of radical polymerizing monomers, starting from the adsorbed photopolymerization initiator, by irradiation with UV light at a wavelength of 300 nm to 400 nm to grow polymer chains on the surface of the object to be modified.

Preferably, the rubber vulcanizate or thermoplastic elastomer contains an allylic carbon atom which is a carbon atom adjacent to a double bond.

The photopolymerization initiator is preferably a benzophenone compound represented by the following formula (1):

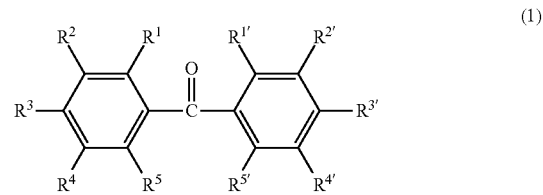

wherein $R^1$ to $R^5$ and $R^{1'}$ to $R^{5'}$ are the same as or different from one another and each represent a hydrogen atom, an alkyl group, a halogen, a hydroxy group, a primary, secondary, or tertiary amino group, a mercapto group, or a hydrocarbon group that may contain an oxygen atom, a nitrogen atom, or a sulfur atom; and any two adjacent groups thereof may be joined to each other to form a cyclic structure together with the carbon atoms to which they are bonded.

Preferably, the Step 2 comprises adding a reducing agent or an antioxidant for the radical polymerization.

The reducing agent or antioxidant is preferably riboflavin, ascorbic acid, α-tocopherol, β-carotene, or uric acid.

Preferably, an inert gas is inserted into a reaction container and a reaction solution during or before the light irradiation so that polymerization is performed in an atmosphere replaced with the inert gas.

The monomers are preferably ionic monomers.

The ionic monomers are preferably at least one selected from the group consisting of acrylic acid and methacrylic acid.

Preferably, the monomers are represented by the following formula:

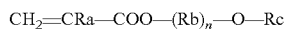

CH$_2$=CRa—COO—(Rb)$_n$—O—Rc wherein Ra represents a hydrogen atom, a methyl group, an ethyl group, or a propyl group; Rb represents a methyl group, an ethyl group, or a propyl group; Rc represents a hydrogen atom, a methyl group, or an ethyl group; and n represents an integer of 1 to 15.

The monomers are preferably fluoro group-containing monomers.

The monomers are preferably fluoroalkyl-containing monomers.

The fluoroalkyl-containing monomers are preferably at least one selected from the group consisting of 3,3,4,4,5,5,6,6,7,7,8,8,9,9,10,10,11,11,12,12,12-heneicosafluorododecyl acrylate (H$_2$C=CHCO$_2$CH$_2$CH$_2$(CF$_2$)$_9$CF$_3$), 3,3,4,4,5,5,6,6,7,7,8,8,9,9,10,10,10-heptadecafluorodecyl acrylate (H$_2$C=CHCO$_2$CH$_2$CH$_2$(CF$_2$)$_7$CF$_3$), 3-(perfluorobutyl)-2-hydroxypropyl acrylate (F(CF$_2$)$_4$CH$_2$CH(OH)CH$_2$OCOCH=CH$_2$), 3-perfluorohexyl-2-hydroxypropyl acrylate (F(CF$_2$)$_6$CH$_2$CH(OH)CH$_2$OCOCH=CH$_2$), 3-(perfluoro-3-methylbutyl)-2-hydroxypropyl acrylate ((CF$_3$)$_2$CF(CF$_2$)$_2$CH$_2$CH(OH)CH$_2$OCOCH=CH$_2$), and 3-(perfluoro-5-methylhexyl)-2-hydroxypropyl acrylate ((CF$_3$)$_2$CF(CF$_2$)$_4$CH$_2$CH(OH)CH$_2$OCOCH=CH$_2$).

The fluoroalkyl-containing monomers are preferably at least one selected from the group consisting of compounds represented by the following formulae (3), (4), (5), and (6):

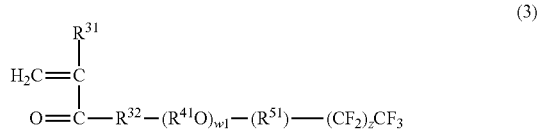

(3)

wherein R$^{31}$ represents a hydrogen atom, a methyl group, an ethyl group, or a propyl group; R$^{32}$ represents —O— or —NH—; R$^{41}$ represents a methylene group, an ethylene group, or a propylene group; R$^{51}$ represents a ketone group and may be absent; w1 represents an integer of 1 to 100; and z represents an integer of 1 to 6,

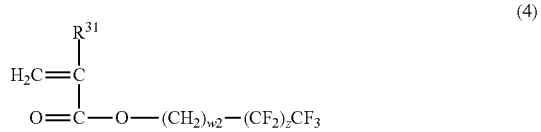

(4)

wherein R$^{31}$ represents a hydrogen atom, a methyl group, an ethyl group, or a propyl group; w2 represents an integer of 4 to 10; and z represents an integer of 1 to 6,

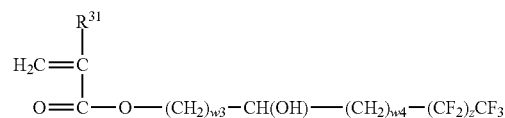

(5)

wherein R$^{31}$ represents a hydrogen atom, a methyl group, an ethyl group, or a propyl group; w3 and w4 each independently represent an integer of 1 to 6; and z represents an integer of 1 to 6,

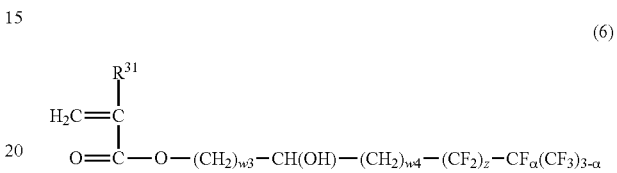

(6)

wherein R$^{31}$ represents a hydrogen atom, a methyl group, an ethyl group, or a propyl group; w3 and w4 each independently represent an integer of 1 to 6; z represents an integer of 1 to 6; and α represents an integer of 1 or 2.

The fluoro group is preferably a fluoroalkylene oxide group or a fluorobenzyl group.

The fluoro group-containing monomers are preferably at least one selected from the group consisting of [1H,1H-perfluoro(2,5-dimethyl-3,6-dioxanonanoyl)]acrylate, 1H,1H-perfluoro(2,5-dimethyl-3,6-dioxanonanoyl)]methacrylate, pentafluorobenzyl acrylate, pentafluorobenzyl methacrylate, and 2,3,5,6-tetrafluorophenyl methacrylate.

Preferably, the (liquid) radical polymerizable monomers or a solution thereof contains a polymerization inhibitor, and the monomers are polymerized in the presence of the polymerization inhibitor.

The polymerization inhibitor is preferably 4-methylphenol.

The polymer chains are preferably 10 to 50000 nm in length.

The present invention also relates to a surface-modified elastic body, which is obtained by the aforementioned surface modification method.

The present invention also relates a surface-modified elastic body, which needs to have sliding properties, low friction, or low water resistance in the presence of water or in a dry state, and which is obtained by the aforementioned surface modification method.

The present invention also relates to a surface-modified elastic body, which is a three-dimensional solid having at least partially a surface modified by the aforementioned surface modification method. The surface-modified elastic body is preferably a polymer brush.

The present invention also relates to a gasket for syringes, which has at least partially a surface modified by the aforementioned surface modification method.

The present invention also relates to a catheter, which has at least partially a surface modified by the aforementioned surface modification method.

The present invention also relates to a tire, which has at least partially a groove surface modified by the aforementioned surface modification method.

The present invention also relates to a tire, which comprises a sidewall having at least partially a surface modified by the aforementioned surface modification method.

Advantageous Effects of Invention

The present invention provides a surface modification method for modifying a rubber vulcanizate or a thermoplastic elastomer as an object to be modified, the method including:

Step 1 of allowing a photopolymerization initiator to be adsorbed on a surface of the object to be modified; and Step 2 of radical polymerizing monomers, starting from the adsorbed photopolymerization initiator, by irradiation with UV light at a wavelength of 300 nm to 400 nm to grow polymer chains on the surface of the object to be modified. The method can impart excellent sliding properties and durability against repeated sliding motion and also provide favorable sealing properties to the surface of the object to be modified. Therefore, by forming polymer chains on the surface of the object to be modified by the method, surface-modified elastic bodies, such as gaskets for syringes, and catheters, which are excellent in the aforementioned performances can be provided. Moreover, since the surface-modified elastic bodies do not have a PTFE polymer structure, they can be sterilized by radiation including gamma rays. Furthermore, by introducing silver, the surface-modified elastic bodies are imparted with antibacterial properties.

DESCRIPTION OF EMBODIMENTS

Figure 1:
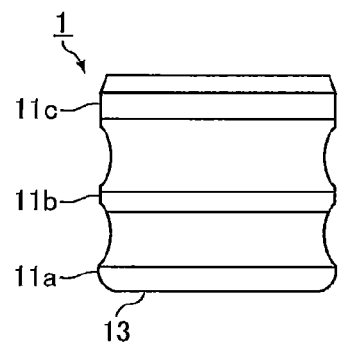
FIG. 1 is a side view of one embodiment of gaskets for syringes.

The surface modification method according to the present invention is a surface modification method for modifying a rubber vulcanizate or a thermoplastic elastomer as an object to be modified, the method including:

Step 1 of allowing a photopolymerization initiator to be adsorbed on a surface of the object to be modified; and Step 2 of radical polymerizing monomers, starting from the adsorbed photopolymerization initiator, by irradiation with UV light at a wavelength of 300 nm to 400 nm to grow polymer chains on the surface of the object to be modified.

In the Step 1, a photopolymerization initiator is allowed to be adsorbed on the surface of vulcanization-molded rubber or molded thermoplastic elastomer (object to be modified) to form polymerization initiation points.

Preferred examples of the rubber vulcanizate and the thermoplastic elastomer include those containing a carbon atom adjacent to a double bond (allylic carbon atom).

Examples of the rubber for the object to be modified include diene rubbers such as styrene-butadiene rubber, butadiene rubber, isoprene rubber, natural rubber, and deproteinized natural rubber; and butyl rubber and halogenated butyl rubber which have a degree of unsaturation of a few percent of isoprene units. In the case of the butyl rubber or halogenated butyl rubber, rubber cross-linked by triazine is preferred because the amount of matter extracted from the rubber vulcanizate is small. In this case, the rubber may contain an acid acceptor, and examples of suitable acid acceptors include hydrotalcites and magnesium carbonate.

In the case of other rubbers, sulfur vulcanization is preferred. In such a case, compounding agents commonly used for sulfur vulcanization may be added, such as vulcanization accelerators, zinc oxide, fillers, and silane coupling agents.

Preferred examples of the fillers include carbon black, silica, clay, talc, and calcium carbonate.

The vulcanization conditions for rubber may be appropriately set. The vulcanization temperature for rubber is preferably 150° C. or higher, more preferably 170° C. or higher, and further preferably 175° C. or higher.

Examples of the thermoplastic elastomer include polymer compounds having rubber elasticity at room temperature owing to the aggregates of plastic components (hard segments) that serve as crosslinking points (e.g. thermoplastic elastomers (TPE) such as styrene-butadiene-styrene copolymers); and polymer compounds having rubber elasticity, obtained by mixing a thermoplastic component and a rubber component and dynamically crosslinking the mixture by a crosslinking agent (e.g. thermoplastic elastomers (TPV) such as polymer alloys containing a styrenic block copolymer or olefinic resin together with a crosslinked rubber component).

Other suitable examples of the thermoplastic elastomer include nylon, polyester, polyurethane, polypropylene, and dynamically-crosslinked thermoplastic elastomers thereof. In the case of dynamically-crosslinked thermoplastic elastomers, preferred are those obtained by dynamically crosslinking halogenated butyl rubber in a thermoplastic elastomer. Here, the thermoplastic elastomer is preferably nylon, polyurethane, polypropylene, or SIBS (styrene-isobutylene-styrene block copolymer), for example.

For example, polymerization initiation points can be formed by adsorption of a photopolymerization initiator on the surface of the object to be modified. Irradiation with light such as UV rays is not necessary. Examples of the photopolymerization initiator include carbonyl compounds, organic sulfur compounds (e.g. tetraethylthiuramdisulfide), persulfides, redox compounds, azo compounds, diazo compounds, halogen compounds, and photoreductive pigments. Preferred among these are carbonyl compounds.

The carbonyl compound as a photopolymerization initiator is preferably benzophenone or its derivative, and suitable examples thereof include benzophenone compounds represented by the following formula (1):

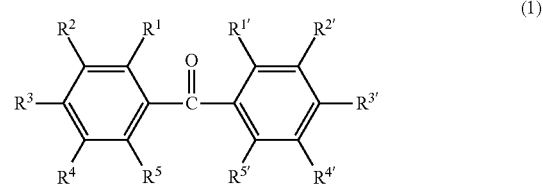

(1)

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary, secondary, or tertiary amino group, a mercapto group, or a hydrocarbon group that may contain an oxygen atom, a nitrogen atom, or a sulfur atom; and any two adjacent groups thereof may be joined to each other to form a cyclic structure together with the carbon atoms to which they are bonded.

Specific examples of the benzophenone compounds include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because they contribute to favorable polymer brushes.

Fluorobenzophenone compounds may also be suitably used as the benzophenone compound. Examples thereof include 2,3,4,5,6-pentafluorobenzophenone and decafluorobenzophenone respectively represented by the following formulae.

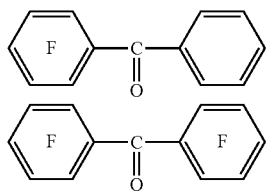

The adsorption of a photopolymerization initiator (e.g. benzophenone compounds) on the surface of the object to be modified may be achieved as follows. In the case of using, for example, a benzophenone compound, the benzophenone compound is dissolved in an organic solvent to prepare a solution; a surface portion of the target object to be modified is treated with this solution so that the compound is adsorbed on the surface portion; and if necessary, the organic solvent is dried to be evaporated off, whereby polymerization initiation points are formed. The surface-treating method is not particularly limited as long as the benzophenone compound solution can be brought into contact with the surface of the object to be modified. Suitable examples thereof include application of the benzophenone compound solution, spraying thereof, and immersion of the surface into the solution. If only a part of the surface needs to be modified, it is sufficient to adsorb the photopolymerization initiator only on such a part of the surface. In this case, for example, application of the solution or spraying of the solution is suitable. Examples of the solvent include methanol, ethanol, acetone, benzene, toluene, methyl ethyl ketone, ethyl acetate, and THF. Acetone is preferred because it does not swell the object to be modified and it is rapidly dried and evaporated off.

In the Step 2, monomers are radical polymerized, starting from the adsorbed photopolymerization initiator, by irradiation with UV light at a wavelength of 300 nm to 400 nm to grow polymer chains on the surface of the object to be modified.

Examples of the monomers include, though not limited to, ionic monomers, monomers represented by the following formula:

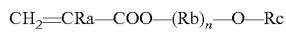

CH$_2$=CRa—COO—(Rb)$_n$—O—Rc (wherein Ra represents a hydrogen atom, a methyl group, an ethyl group, or a propyl group; Rb represents a methyl group, an ethyl group, or a propyl group; Rc represents a hydrogen atom, a methyl group, or an ethyl group; and n represents an integer of 1 to 15), and fluoro group-containing monomers. Examples of the monomers represented by that formula include 2-methoxyethyl acrylate, and 2-methoxymethyl methacrylate.

Examples of the ionic monomers include acrylic acid, acrylic acid alkali metal salts (sodium acrylate, potassium acrylate, etc.), acrylic silver, amine salts of acrylic acid; methacrylic acid, methacrylic acid alkali metal salts (sodium methacrylate, potassium methacrylate, etc.), methacrylic silver, amine salts of methacrylic acid, and zwitterionic monomers. Each of these may be used alone, or two or more of these may be used in combination. Acrylic acid and methacrylic acid are preferred among the examples.

Examples of the zwitterionic monomers (zwitterionic group-containing compounds: compounds having permanent positive and negative charge centers) include carboxybetaines, sulfobetaines, and phosphorbetaines. From the viewpoint that excellent sliding properties and durability are achieved while favorable sealing properties are maintained, compounds represented by formula (7) below may be used as the zwitterionic monomer, and compounds represented by formula (8) below are suitable among these.

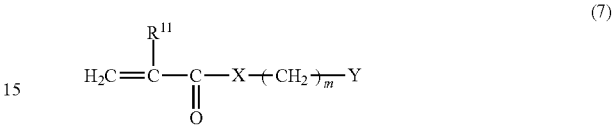

In the formula, $R^{11}$ represents —H or —CH$_3$; X represents —O— or —NH—; m represents an integer of 1 or larger; and Y represents a zwitterionic group.

In the formula (7), preferably, $R^{11}$ is —CH$_3$; X is —O—, and m is an integer of 1 to 10. Regarding the zwitterionic group represented by Y, examples of the cation include quaternary ammoniums such as tetraalkylammoniums, and examples of the anion include carboxylates, sulfonates, and phosphates.

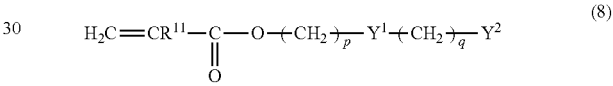

In the formula, $R^{11}$ represents —H or —CH$_3$; p and q each represent an integer of 1 or larger; and $Y^1$ and $Y^2$ represent ionic functional groups having opposite electric charges to each other.

In the formula (8), p is preferably an integer of 2 or larger, and more preferably an integer of 2 to 10. q is preferably an integer of 1 to 10, and more preferably an integer of 2 to 4. Preferred examples of $R^{11}$ are the same as mentioned above. The aforementioned cations and anions may be mentioned as $Y^1$ and $Y^2$.

Preferred typical examples of the zwitterionic monomers include compounds represented by the following formulae (8-1) to (8-4):

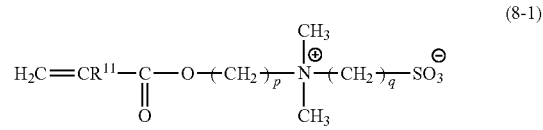

wherein $R^{11}$ represents a hydrogen atom or a methyl group; and p and q each represent an integer of 1 to 10,

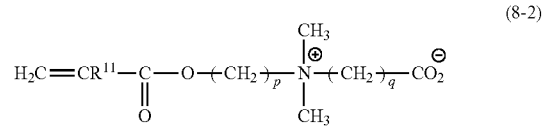

wherein $R^{11}$ represents a hydrogen atom or a methyl group; and p and q each represent an integer of 1 to 10, (8-3)

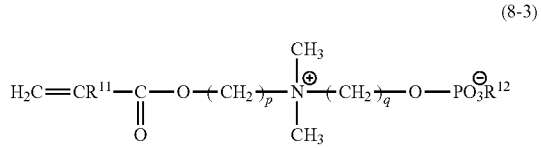

wherein $R^{11}$ represents a hydrogen atom or a methyl group; $R^{12}$ represents a C1-C6 hydrocarbon group; and p and q each represent an integer of 1 to 10, and (8-4)

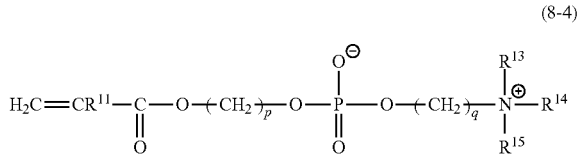

wherein $R^{11}$ represents a hydrogen atom or a methyl group; $R^{13}$, $R^{14}$, and $R^{15}$ are the same as or different from one another and each represent a C1 or C2 hydrocarbon group; and p and q each represent an integer of 1 to 10.

Examples of the compounds represented by the formula (8-1) include dimethyl(3-sulfopropyl)(2-(meth)acryloyloxyethyl)ammonium betaine. Examples of the compounds represented by the formula (8-2) include dimethyl(2-carboxyethyl)(2-(meth)acryloyloxyethyl)ammonium betaine. Examples of the compounds represented by the formula (8-3) include dimethyl(3-methoxyphosphopropyl)(2-(meth)acryloyloxyethyl)ammonium betaine. Examples of the compounds represented by the formula (8-4) include 2-(meth)acryloyloxyethyl phosphorylcholine. Examples of the zwitterionic monomers also include 2-(meth)acryloyloxyethyl carboxybetaine, and 2-(meth)acryloyloxyethyl sulfobetaine. Among these, 2-(meth)acryloyloxyethyl phosphorylcholine is particularly preferred from the viewpoint of high biocompatibility, i.e. low protein adsorbability.

Examples of the fluoro group-containing monomers include fluoroalkyl-containing monomers. Usable fluoroalkyl-containing monomers are not particularly limited as long as they are compounds each having one radical polymerizable group such as a vinyl group and at least one fluoroalkyl group. The "fluoroalkyl group" herein refers to an alkyl group in which at least one hydrogen atom is replaced with a fluorine atom, and is preferably a C7-C30 fluoroalkyl group, and especially preferably a C7-C30 fluoroalkyl group having a perfluoroalkyl group at the end thereof.

The fluoroalkyl-containing monomer preferably has a fluorine atom content of not less than 45% by mass, more preferably not less than 50% by mass, of the molecular weight of the monomer.

Compounds represented by A-B (wherein A represents a radical polymerizable group, and B represents a fluoroalkyl group) can be suitably used as the fluoroalkyl-containing monomer. Examples thereof include those represented by the following formula:

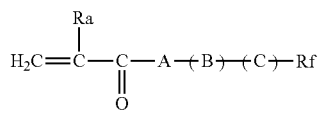

wherein Ra represents a hydrogen atom, a methyl group, an ethyl group, or a propyl group; A represents —O— or —NH—; B represents an optionally substituted alkylene or polyoxyalkylene group and may be absent; C represents a ketone group and may be absent; and Rf represents an optionally substituted fluoroalkyl group.

The number of carbon atoms of the alkylene group represented by B is preferably 1 to 15. The polyoxyalkylene group is shown by $(RO)_w$; preferably, the number of carbon atoms of R is 1 to 10 and the polymerization degree w is 1 to 150. The alkylene or polyoxyalkylene group may have a substituent group. Moreover, Rf is preferably a C2-C40 fluoroalkyl group having a perfluoroalkyl group at the end thereof, and may have a substituent group. Examples of the substituent groups for B and Rf include, though not limited to, a hydroxyl group.

From the viewpoint of easy polymerizability, the fluoroalkyl-containing monomer is preferably a compound represented by the following formula (2):

(2)

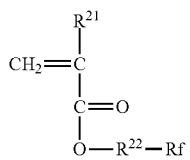

wherein $R^{21}$ represents a hydrogen atom, a methyl group, an ethyl group, or a propyl group; $R^{22}$ represents a C1-C4 alkylene group; and Rf represents a C7-C30 fluoroalkyl group having a perfluoroalkyl group at the end thereof.

$R^{21}$ is preferably a hydrogen atom or a methyl group. $R^{22}$ is preferably a C1-C3 alkylene group. Rf is preferably a C7-C20 fluoroalkyl group having a perfluoroalkyl group at the end thereof.

Suitable examples of the compound represented by the formula (2) include (meth)acrylate compounds represented by the following formulae (2-1) to (2-3):

(2-1)

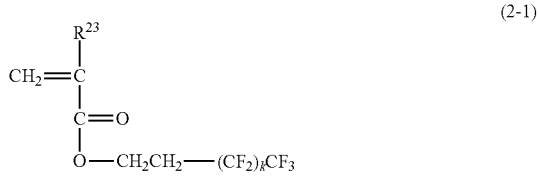

(2-2)

(2-3)

wherein $R^{23}$ represents a hydrogen atom or a methyl group; and k represents 7, 8, 9, 10, 11, or 12.

Specific examples of the fluoroalkyl-containing monomers include 3,3,4,4,5,5,6,6,7,7,8,8,9,9,10,10,11,11,12,12,12-heneicosafluorododecyl acrylate ($H_2C$=$CHCO_2CH_2CH_2$ $(CF_2)_9CF_3$), 3,3,4,4,5,5,6,6,7,7,8,8,9,9,10,10,10-heptadecafluorodecyl acrylate ($H_2C$=$CHCO_2CH_2CH_2(CF_2)_7CF_3$), $H_2C$=$CHCO_2CH_2(CF_2)_9CF_3$, $H_2C$=$CHCO_2CH_2(CF_2)_7$ $CF_3$, 3,3,4,4,5,5,6,6,7,7,8,8,9,9,10,10,11,11,12,12,12-henеicosafluorododecyl methacrylate, 3,3,4,4,5,5,6,6,7,7,8,8,9,9,10,10,10-heptadecafluorodecyl methacrylate, 3-(perfluorobutyl)-2-hydroxypropyl acrylate ($F(CF_2)_4CH_2CH(OH)$ $CH_2OCOCH$=$CH_2$), 3-perfluorohexyl-2-hydroxypropyl acrylate ($F(CF_2)_6CH_2CH(OH)CH_2OCOCH$=$CH_2$), 3-(perfluoro-3-methylbutyl)-2-hydroxypropyl acrylate (($CF_3)_2CF$ $(CF_2)_2CH_2CH(OH)CH_2OCOCH$=$CH_2$), and 3-(perfluoro-5-methylhexyl)-2-hydroxypropyl acrylate (($CF_3)_2CF(CF_2)_4$ $CH_2CH(OH)CH_2OCOCH$=$CH_2$). From the viewpoint of lowering the surface free energy, i.e. providing better sliding properties, preferred among the examples are 3,3,4,4,5,5,6,6,7,7,8,8,9,9,10,10,10-heptadecafluorodecyl acrylate ($H_2C$=$CHCO_2CH_2CH_2(CF_2)_7CF_3$), 3-(perfluorobutyl)-2-hydroxypropyl acrylate ($F(CF_2)_4CH_2CH(OH)$ $CH_2OCOCH$=$CH_2$), 3-perfluorohexyl-2-hydroxypropyl acrylate ($F(CF_2)_6CH_2CH(OH)CH_2OCOCH$=$CH_2$), 3-(perfluoro-3-methylbutyl)-2-hydroxypropyl acrylate (($CF_3)_2CF$ $(CF_2)_2CH_2CH(OH)CH_2OCOCH$=$CH_2$), and 3-(perfluoro-5-methylhexyl)-2-hydroxypropyl acrylate (($CF_3)_2CF(CF_2)_4$ $CH_2CH(OH)CH_2OCOCH$=$CH_2$). Each of these may be used alone, or two or more of these may be used in combination.

Vinyl monomers each having a fluoroalkyl group at a side chain may be used as the fluoroalkyl-containing monomer. Among the vinyl monomers, monomers each having a fluoroalkyl group at the end of a side chain and an oxyalkylene group at a site close to the double bond side are preferred. Specifically, monomers represented by formula (3) below can be suitably used.

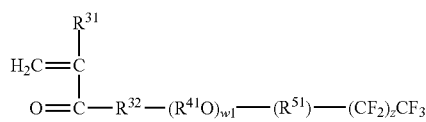

(3)

In the formula (3), $R^{31}$ represents a hydrogen atom, a methyl group, an ethyl group, or a propyl group; $R^{32}$ represents —O— or —NH—; $R^{41}$ represents a methylene group, an ethylene group, or a propylene group; $R^{51}$ represents a ketone group and may be absent; w1 represents an integer of 1 to 100; and z represents an integer of 1 to 6.

Moreover, suitable examples of the fluoroalkyl-containing monomers also include monomers represented by the following formulae (4), (5), and (6):

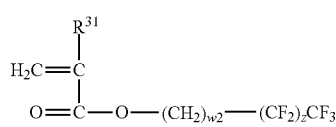

(4)

wherein $R^{31}$ represents a hydrogen atom, a methyl group, an ethyl group, or a propyl group; w2 represents an integer of 4 to 10; and z represents an integer of 1 to 6,

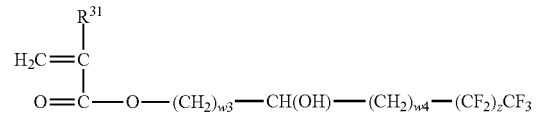

(5)

wherein $R^{31}$ represents a hydrogen atom, a methyl group, an ethyl group, or a propyl group; w3 and w4 each independently represent an integer of 1 to 6; and z represents an integer of 1 to 6, and

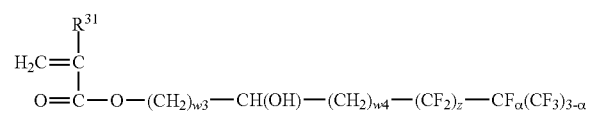

(6)

wherein $R^{31}$ represents a hydrogen atom, a methyl group, an ethyl group, or a propyl group; w3 and w4 each independently represent an integer of 1 to 6; z represents an integer of 1 to 6; and α represents an integer of 0 to 2.

Preferably, when a structure with high molecular mobility, such as $(R^{41}O)_{w1}$ or $(CH_2)_{w2}$, is located between $CH_2$=$CR^{31}$, which forms a main chain by polymerization, and a fluoroalkyl group of $(CF_2)_zCF_3$, the $(CF_2)_zCF_3$ or $CF_3$ group tends to be localized on the surface under dry conditions, thereby enhancing the sliding properties. Moreover, preferably, when a structure capable of hydrogen bonding, such as OH, COOH, C=O, and NH groups, is located between $CH_2$=$CR^{31}$, which forms a main chain by polymerization, and a fluoroalkyl group of $(CF_2)_zCF_3$, the side chains are restrained so that the group $(CF_2)_zCF_3$ or $CF_3$ tends to be fixed or localized on the surface even under dry conditions, thereby enhancing the sliding properties.

Other preferred specific examples of the fluoro group-containing monomers include [1H,1H-perfluoro(2,5-dimethyl-3,6-dioxanonanoyl)]acrylate, [1H,1H-perfluoro(2,5-dimethyl-3,6-dioxanonanoyl)]methacrylate, pentafluorobenzyl acrylate, pentafluorobenzyl methacrylate, and 2,3,5,6-tetrafluorophenyl methacrylate, which are respectively represented by the following formulae:

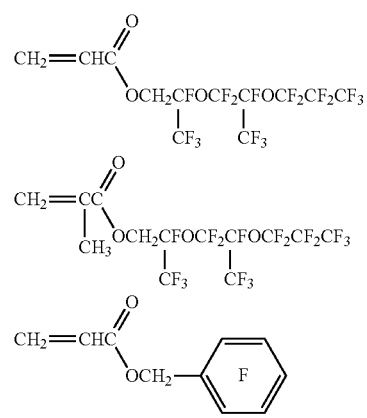

-continued

CH₂=C(CH₃)C(=O)OCH₂-[phenyl]-F

CH₂=C(CH₃)C(=O)O-[phenyl]-F-H.

An example of the method of radical polymerizing monomers in the Step 2 is as follows. First, (liquid) monomers or a solution thereof is applied (sprayed) to the surface of the object to be modified on which a benzophenone compound or the like is adsorbed, or the object to be modified is immersed into (liquid) monomers or a solution thereof. Then, irradiation with UV light is performed so that radical polymerization (photoradical polymerization) of each form of monomers proceeds, whereby polymer chains are grown on the surface of the object to be modified. Alternatively, after the above application, the surface of the object to be modified may be covered with a transparent glass, PET, polycarbonate, or the like. Then, irradiation with light such as ultraviolet rays is performed thereon so that radical polymerization (photoradical polymerization) of each form of monomers proceeds, whereby polymer chains are grown on the surface of the object to be modified.

In the Step 2, it is preferable to allow radical polymerization (photoradical polymerization) to proceed by light irradiation to monomers with a reducing agent or an antioxidant added thereto. This arrangement is preferred because the reducing agent or antioxidant scavenges oxygen in the system. In the monomers with a reducing agent or an antioxidant added thereto, the components may be mixed with or may be separated from each other. Alternatively, the reducing agent or antioxidant may be added after the object to be modified obtained in the Step 1 is brought into contact with monomers, or after the object to be modified on which polymer chains are formed is brought into contact with other monomers. Or alternatively, the components may be mixed in advance before the mixed material is brought into contact with the object to be modified or the object to be modified on which polymer chains are formed.

Specifically, for example, first, the object to be modified on the surface of which polymerization initiation points are formed from the photopolymerization initiator, obtained in the Step 1, is brought into contact (e.g. immersion, application) with (liquid) monomers or a solution thereof to which a solution of a reducing agent or an antioxidant is added. Alternatively, the object to be modified is brought into contact with (liquid) monomers or a solution thereof, and then a solution of a reducing agent or an antioxidant is put on the resulting surface. Next, light irradiation is performed, and then the object to be modified on which polymer chains are formed is subjected to the same process as above using (liquid) monomers or a solution thereof, and a solution of a reducing agent or an antioxidant. In this manner, radical polymerization of each form of monomers is performed so that polymer chains and other polymer chains can be sequentially formed.

For example, since fluoroalkyl-containing monomers have a specific gravity of more than 1, and also do not mix with water, a solution of a reducing agent or an antioxidant is separated and put on the (liquid) radical polymerizable monomers or a solution thereof.

The reducing agent and the antioxidant are not particularly limited, and compounds having a reduction or antioxidant action can be appropriately used. Examples thereof include vitamin A series such as retinol, dehydroretinol, retinol acetate, retinol palmitate, retinal, retinoic acid, and vitamin A oil, and derivatives and salts thereof; carotenoids such as α-carotene, β-carotene, γ-carotene, cryptoxanthin, astaxanthin, and fucoxanthin, and derivatives thereof; vitamin B series such as pyridoxine, pyridoxal, pyridoxal-5-phosphate, and pyridoxamine, and derivatives and salts thereof; vitamin C series such as ascorbic acid, sodium ascorbate, ascorbyl stearate, ascorbyl palmitate, ascorbyl dipalmitate, and magnesium ascorbyl phosphate, and derivatives and salts thereof; vitamin D series such as ergocalciferol, cholecalciferol, and 1,2,5-dihydroxy-cholecalciferol, and derivatives and salts thereof; vitamin E series such as α-tocopherol, β-tocopherol, γ-tocopherol, δ-tocopherol, α-tocotrienol, β-tocotrienol, γ-tocotrienol, δ-tocotrienol, tocopherol acetate, and tocopherol nicotinate, and derivatives and salts thereof; trolox, and derivatives and salts thereof; dihydroxytoluene, butylhydroxytoluene, butylhydroxyanisole, dibutylhydroxytoluene, α-lipoic acid, dehydrolipoic acid, and glutathione, and derivatives and salts thereof; uric acid, and erythorbic acid and their derivatives and salts, such as erythorbic acid and sodium erythorbate; gallic acid, and derivatives and salts thereof, such as gallic acid and propyl gallate; rutin, and derivatives and salts thereof, such as rutin and α-glycosyl-rutin; tryptophan, and derivatives and salts thereof; histidine, and derivatives and salts thereof; cysteine derivatives and salts thereof such as N-acetylcysteine, N-acetylhomocysteine, N-octanoylcysteine, and N-acetylcysteine methyl ester; cystine derivatives and salts thereof such as N,N'-diacetylcystine dimethyl ester, N,N'-dioctanoylcystine dimethyl ester, and N,N'-dioctanoylhomocystine dimethyl ester; carnosine, and derivatives and salts thereof; homocarnosine, and derivatives and salts thereof; anserine, and derivatives and salts thereof; carcinine, and derivatives and salts thereof; dipeptide or tripeptide derivatives containing histidine and/or tryptophan and/or histamine, and salts thereof; flavonoids such as flavanone, flavone, anthocyanin, anthocyanidin, flavonol, quercetin, quercitrin, myricetin, fisetin, hamamelitannin, catechin, epicatechin, gallocatechin, epigallocatechin, epicatechin gallate, and epigallocatechin gallate; tannic acid, caffeic acid, ferulic acid, protocatechuic acid, calcone, oryzanol, carnosol, sesamol, sesamine, sesamolin, zingerone, curcumin, tetrahydrocurcumin, clovamide, deoxyclovamide, shogaol, capsaicine, vanillylamide, ellagic acid, bromphenol, flavoglaucin, melanoidin, riboflavin, riboflavin butyrate, flavin mononucleotide, flavin adenine nucleotide, ubiquinone, ubiquinol, mannitol, bilirubin, cholesterol, ebselen, selenomethionine, ceruloplasmin, transferrin, lactoferrin, albumin, superoxide dismutase, catalase, glutathione peroxidase, metallothionein, and O-phosphono-pyridoxylidene rhodamine. Each of these may be used alone, or two or more of these may be used in combination.

Preferred among these are riboflavin, ascorbic acid, α-tocopherol, β-carotene, and uric acid, and particularly preferred are riboflavin and ascorbic acid, because of their high oxygen scavenging capability.

In the case of using a solution of a reducing agent or an antioxidant, the concentration of the reducing agent or antioxidant is preferably $10^{-4}$ to 1% by mass, and more preferably $10^{-3}$ to 0.1% by mass.

The amount of the radical polymerizable monomers may be appropriately adjusted depending on, for example, a desired length of polymer chains to be formed and desired performance to be achieved by the chains. Also, the amount of the reducing agent or antioxidant may be appropriately adjusted from the viewpoint of the oxygen scavenging capability in the system, for example.

With respect to the solvent to be applied (sprayed), the method for applying (spraying), the method for immersion, the conditions for irradiation, and the like, conventionally known materials and methods may be used. The solution of radical polymerizable monomers may be an aqueous solution or a solution prepared by dissolving the monomers in an organic solvent that does not dissolve a photopolymerization initiator (e.g. benzophenone compounds) to be used. Furthermore, the (liquid) radical polymerizable monomers or a solution thereof may contain a known polymerization inhibitor such as 4-methylphenol.

In the present invention, radical polymerization of monomers is allowed to proceed by light irradiation after the (liquid) monomers or a solution thereof is applied to the object to be modified, or after the object to be modified is immersed in the (liquid) monomers or a solution thereof. Here, UV light sources can be suitably used, such as high-pressure mercury lamps, metal halide lamps, and LED lamps, each of which has an emission wavelength mainly in the range of ultraviolet rays. The light dose may be appropriately adjusted in consideration of the polymerization time and uniform progress of the reaction. In order to prevent polymerization inhibition due to active gas such as oxygen in a reaction container, it is preferable to remove oxygen in the reaction container and the reaction solution during or before light irradiation. Thus, for example, a method may appropriately be employed in which inert gas such as nitrogen gas or argon gas is inserted into the reaction container and the reaction solution to discharge active gas such as oxygen from the reaction system to replace the atmosphere in the reaction system with the inert gas. In addition, in order to prevent reaction inhibition due to oxygen or the like, for example, measures may appropriately be used in which a UV light source is placed such that no air layer (oxygen content: 15% or higher) exists between the reaction container made of glass, plastics or the like and the reaction solution or the object to be modified.

The wavelength of ultraviolet rays is at 300 to 400 nm. This enables the polymer chains to be favorably formed on the surface of the object to be modified. The light source may be a high-pressure mercury lamp, an LED with a center wavelength of 365 nm, an LED with a center wavelength of 375 nm, or the like. More preferred is irradiation with LED light at 355 to 380 nm. Especially, from the viewpoint of efficiency, preferred are LEDs with a center wavelength of 365 nm which is close to the excitation wavelength (366 nm) of benzophenone, for example.

The length of the polymer chains formed in the Step 2 is preferably 10 to 50000 nm, and more preferably 100 to 50000 nm. Chains shorter than 10 nm are unlikely to provide good sliding properties. Chains longer than 50000 nm are unlikely to be expected to provide better sliding properties and thus are likely to increase the cost of raw materials because expensive monomers are used. In addition, a surface pattern formed by the surface treatment is likely to be visible to the naked eye, which tends to damage the appearance and to decrease the sealing properties.

In the Step 2, two or more species of monomers may be simultaneously radical polymerized starting from the polymerization initiation points. Moreover, multiple kinds of polymer chains may be grown on the surface of the object to be modified. The surface modification method of the present invention may include cross-linking between polymer chains. In this case, ionic cross-linking, cross-linking by a hydrophilic group containing an oxygen atom, or cross-linking by a halogen group (e.g. iodine), may be carried out between the polymer chains.

Application of the surface modification method to a rubber vulcanizate or a thermoplastic elastomer enables to provide a surface-modified elastic body. For example, a surface-modified elastic body excellent in sliding properties in the presence of water or in a dry state can be obtained. This surface-modified elastic body is also excellent in that it shows low friction and low water resistance or drag. Moreover, application of the method to at least part of a three-dimensional solid (e.g. elastic body) enables to provide a surface-modified elastic body. Preferred examples of the surface-modified elastic body include polymer brushes. The polymer brush herein means a graft polymer obtained by the "grafting from" approach by surface-initiated living radical polymerization. The graft chains are preferably oriented in a direction substantially vertical to the surface of the object to be modified because, in such a case, the entropy is reduced and the molecular mobility of the graft chains is reduced, which ensures sliding properties. Preferred are semidilute brushes and concentrated brushes which have a brush density of 0.01 chains/nm$^2$ or higher.

Furthermore, application of the surface modification method to a rubber vulcanizate or a thermoplastic elastomer enables to produce a gasket for syringes or a catheter which has at least partially a modified surface. The modification is preferably performed at least on the sliding portion of the gasket or catheter surface, and it may be performed on the entire surface.

FIG. 1 is a side view of one embodiment of gaskets for syringes. A gasket 1 shown in FIG. 1 has three circular protruding portions 11$a$, 11$b$, and 11$c$, continuously protruding in the circumferential direction, on the outer periphery that is to be in contact with the inner periphery of a syringe barrel. Examples of the portion of the gasket 1 to which the surface modification is applied include (1) the surface of protruding portions that is to be in contact with a syringe barrel, such as the circular protruding portions 11$a$, 11$b$, and 11$c$; (2) the entire side surface including the circular protruding portions 11$a$, 11$b$, and 11$c$; and (3) the entire side surface and a bottom surface 13.

Furthermore, application of the surface modification method to grooves formed on the tread of a tire for use on vehicles such as passenger cars to form a polymer brush on the grooves enables to reduce the fluid resistance of the groove surface on wet or snowy roads and to increase the contact angle with water. Therefore, the abilities to remove and drain water or snow are enhanced and the grip performance is improved. Moreover, application of the surface modification method to sidewalls of a tire to form a polymer brush on the sidewall portion enables to make the sidewalls stain-resistant.

Figure 2:
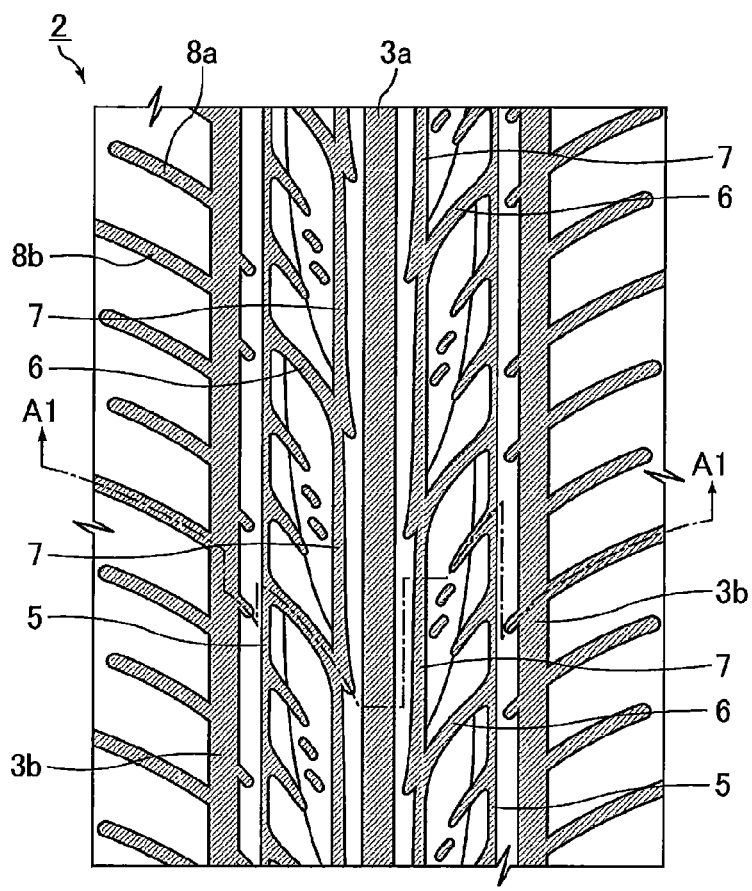
FIG. 2 is a development view of one example of the tread portion of pneumatic tires (the whole tire is not illustrated).
Figure 3:
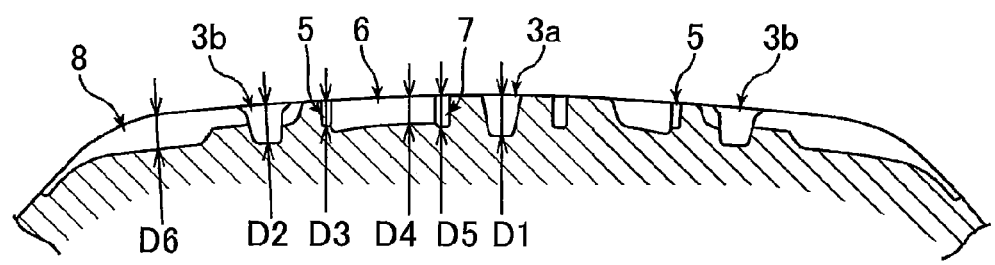
FIG. 3 is an A1-A1 cross-sectional view of the example of FIG. 2.

FIG. 2 is a development view of one example of the tread portion 2 of a pneumatic tire (the whole tire is not illustrated). FIG. 3 is an A1-A1 cross-sectional view of the example of FIG. 2.

In FIGS. 2 and 3, a longitudinal center groove 3$a$ (groove depth D1) and longitudinal shoulder grooves 3$b$ (groove depth D2) are straight grooves straightforwardly extending in the tire circumferential direction. Such straight grooves may contribute to low resistance to drainage and high drainage performance upon straight running.

The pneumatic tire also has fine grooves 5 (groove depth D3) extending in the tire circumferential direction on the side of the longitudinal shoulder groove 3$b$; beveled intermediate grooves 6 (groove depth D4) extending with an inclination from the fine groove 5 toward the longitudinal center groove 3a; connecting grooves 7 (groove depth D5) located at positions inner than the fine grooves 5 in the tire axis direction and connecting the beveled intermediate grooves 6 next to one another in the tire circumferential direction; and lateral shoulder grooves 8, 8a, and 8b (groove depth D6) extending from the longitudinal shoulder groove 3b toward the outside of the tire; and the like, and these grooves may also contribute to drainage performance. Application of the above method to these grooves enables to produce the aforementioned effects.

EXAMPLES

The following will describe the present invention in more detail based on, though not limited to, examples.

Example 1

A chlorobutyl rubber (degree of unsaturation: 1 to 2%) having isoprene units was cross-linked by triazine to give a rubber vulcanizate (vulcanized at 180° C. for 10 minutes). The rubber vulcanizate was immersed in an acetone solution of benzophenone (3 wt %) so that the benzophenone was adsorbed onto the surface of the rubber vulcanizate. Then, the rubber vulcanizate was dried to remove acetone.

The dried rubber vulcanizate was immersed in an acrylic acid aqueous solution (2.5 M: 18 g of acrylic acid was dissolved in 100 mL of water) in a glass reaction container, and the reaction container was sealed with a rubber. Then, argon gas was inserted into the reaction container, followed by bubbling for 15 minutes to remove oxygen. Irradiation with ultraviolet rays was then performed for one hour using an LED light at a wavelength of 365 nm to cause radical polymerization so that polymer chains were grown. In this manner, a surface-modified elastic body (polymer brush) was obtained.

Example 2

A surface-modified elastic body (polymer brush) was obtained in the same manner as in Example 1, except that an acetone solution of benzophenone (3 wt %) was applied to the surface of the rubber vulcanizate so that the benzophenone was adsorbed.

Example 3

A surface-modified elastic body (polymer brush) was obtained in the same manner as in Example 1, except that the surface of the rubber vulcanizate was immersed in an acetone solution of benzophenone (1 wt %) so that the benzophenone was adsorbed on the surface of the rubber vulcanizate.

Example 4

A surface-modified elastic body (polymer brush) was obtained in the same manner as in Example 1, except that an acetone solution of benzophenone (1 wt %) was applied to the surface of the rubber vulcanizate so that the benzophenone was adsorbed on the surface of the rubber vulcanizate.

Comparative Example 1

A rubber vulcanizate (vulcanized at 180° C. for 10 minutes) prepared by cross-linking a chlorobutyl rubber by triazine was used.

The surface-modified elastic bodies prepared in the examples and the comparative example were evaluated by the following methods.

(Length of Polymer Chains)

The length of polymer chains formed on the surface of the rubber vulcanizate was measured on a cross section of the modified rubber vulcanizate with polymer chains formed thereon using an SEM at an accelerating voltage of 15 kV and a magnification of 1000 times. The thickness of the polymer layer photographed was treated as the length of polymer chains.

(Coefficient of Static Friction and Coefficient of Dynamic Friction)

The coefficients of static friction and dynamic friction of the surface of the surface-modified elastic body and the coefficients of static friction and dynamic friction of the surface of the sample with 200 µL of water dripped thereon were measured in conformity with the method described in ASTM D1894. Furthermore, the sample was brought into contact with borosilicate glass and the friction with borosilicate glass was measured. The measurement of the coefficients of friction was performed under the following conditions: load 200 g, tensile rate 600 mm/min, and load distance 10 cm. The device used here was HEIDON type 14 (Shinto Scientific Co., Ltd.).

TABLE 1

| Example No. | | Example 1 | Example 2 | Example 3 | Example 4 | Comparative Example 1 |
|---|---|---|---|---|---|---|
| Length of polymer chains (nm) | | 2100 | 2200 | 1800 | 1600 | None |
| without water dripping | Coefficient of static friction | 0.98 | 0.97 | 0.99 | 1.04 | 2.08 |
| | Coefficient of dynamic friction | 0.46 | 0.46 | 0.52 | 0.57 | 1.73 |
| with water dripping | Coefficient of static friction | 0.74 | 0.78 | 0.82 | 0.85 | 1.90 |
| | Coefficient of dynamic friction | 0.25 | 0.28 | 0.32 | 0.36 | 1.36 |

The results in Table 1 show that the surface of the surface-modified elastic bodies prepared in the examples had greatly reduced coefficients of static friction and dynamic friction, and therefore had good sliding properties. Moreover, since only the surface was modified, the sealing properties of the surface-modified elastic bodies were equal to that in Comparative Example 1.

Thus, in the case that the present invention is applied to gaskets for syringe plungers, sufficient sealing properties are achieved while the friction of the plunger with the syringe barrel is reduced, whereby treatment using such a syringe can be easily and accurately performed. Furthermore, since the difference between the coefficient of static friction and the coefficient of dynamic friction is small, start of pushing the plunger and the subsequent approaching of the plunger can be smoothly performed without pulsation. Similarly, in the case that a syringe barrel is formed from a thermoplastic elastomer and polymer chains are formed on its inner surface, treatment using the syringe can be easily performed.

Furthermore, the aforementioned effects can be expected when polymer chains are formed on the surface of grooves formed on treads, and sidewalls of tires used on vehicles such as passenger cars, or on the surface of diaphragms, sliding surfaces of skis and snowboards, swimsuits, road signs, sign boards, and the like.

REFERENCE SIGNS LIST

1: gasket
11a, 11b, 11c: circular protruding portion
13: bottom surface
2: tread portion
3a: longitudinal center groove
3b: longitudinal shoulder groove
5: fine groove
6: beveled intermediate groove
7: connecting groove
8, 8a, 8b: lateral shoulder groove

The invention claimed is:
1. A surface modification method for modifying a rubber vulcanizate or a thermoplastic elastomer as an object to be modified, wherein said rubber vulcanizate or thermoplastic elastomer contains an allylic carbon atom which is a carbon atom adjacent to a double bond, the method comprising:
Step 1 of allowing a photopolymerization initiator to be adsorbed on a surface of the object to be modified; and
Step 2 of radical polymerizing monomers, starting from the adsorbed photopolymerization initiator, by irradiation with UV light at a wavelength of 300 nm to 400 nm to grow polymer chains on the surface of the object to be modified.
2. The surface modification method according to claim 1, wherein the photopolymerization initiator is a benzophenone compound represented by the following formula (1):

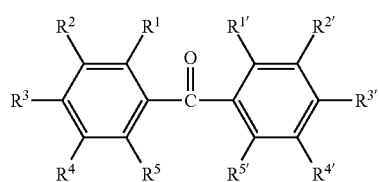

(1)

wherein $R^1$ to $R^5$ and $R^{1'}$ to $R^{5'}$ are the same as or different from one another and each represent a hydrogen atom, an alkyl group, a halogen, a hydroxy group, a primary, secondary, or tertiary amino group, a mercapto group, or a hydrocarbon group that may contain an oxygen atom, a nitrogen atom, or a sulfur atom; and any two adjacent groups thereof may be joined to each other to form a cyclic structure together with the carbon atoms to which they are bonded.
3. The surface modification method according to claim 1, wherein the Step 2 comprises adding a reducing agent or an antioxidant for the radical polymerization.
4. The surface modification method according to claim 3, wherein the reducing agent or antioxidant is riboflavin, ascorbic acid, α-tocopherol, β-carotene, or uric acid.
5. The surface modification method according to claim 1, wherein an inert gas is inserted into a reaction container and a reaction solution during or before the light irradiation so that polymerization is performed in an atmosphere replaced with the inert gas.
6. The surface modification method according to claim 1, wherein the monomers are ionic monomers.
7. The surface modification method according to claim 6, wherein the ionic monomers are at least one selected from the group consisting of acrylic acid and methacrylic acid.
8. The surface modification method according to claim 1, wherein the monomers are represented by the following formula:

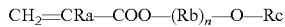

wherein Ra represents a hydrogen atom, a methyl group, an ethyl group, or a propyl group; Rb represents a methyl group, an ethyl group, or a propyl group; Rc represents a hydrogen atom, a methyl group, or an ethyl group; and n represents an integer of 1 to 15.
9. The surface modification method according to claim 1, wherein the monomers are fluoro group-containing monomers.
10. The surface modification method according to claim 9, wherein the monomers are fluoroalkyl-containing monomers.
11. The surface modification method according to claim 10, wherein the fluoroalkyl-containing monomers are at least one selected from the group consisting of
3,3,4,4,5,5,6,6,7,7,8,8,9,9,10,10,11,11,12,12,12-heneicosafluorododecyl acrylate ($H_2C\!=\!CHCO_2CH_2CH_2(CF_2)_9CF_3$),
3,3,4,4,5,5,6,6,7,7,8,8,9,9,10,10,10-heptadecafluorodecyl acrylate ($H_2C\!=\!CHCO_2CH_2CH_2(CF_2)_7CF_3$),
3-(perfluorobutyl)-2-hydroxypropyl acrylate ($F(CF_2)_4CH_2CH(OH)CH_2OCOCH\!=\!CH_2$),
3-perfluorohexyl-2-hydroxypropyl acrylate ($F(CF_2)_6CH_2CH(OH)CH_2OCOCH\!=\!CH_2$),
3-(perfluoro-3-methylbutyl)-2-hydroxypropyl acrylate ($(CF_3)_2CF(CF_2)_2CH_2CH(OH)CH_2OCOCH\!=\!CH_2$), and
3-(perfluoro-5-methylhexyl)-2-hydroxypropyl acrylate ($(CF_3)_2CF(CF_2)_4CH_2CH(OH)CH_2OCOCH\!=\!CH_2$).
12. The surface modification method according to claim 10, wherein the fluoroalkyl-containing monomers are at least one selected from the group consisting of compounds represented by the following formulae (3), (4), (5), and (6):

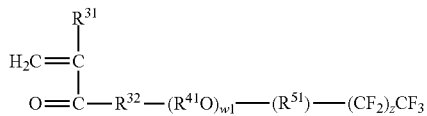

(3)

wherein $R^{31}$ represents a hydrogen atom, a methyl group, an ethyl group, or a propyl group; $R^{32}$ represents —O— or —NH—; $R^{41}$ represents a methylene group, an ethylene group, or a propylene group; $R^{51}$ represents a ketone group and may be absent; w1 represents an integer of 1 to 100; and z represents an integer of 1 to 6,

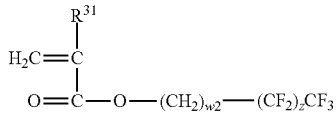 (4)

wherein $R^{31}$ represents a hydrogen atom, a methyl group, an ethyl group, or a propyl group; w2 represents an integer of 4 to 10; and z represents an integer of 1 to 6,

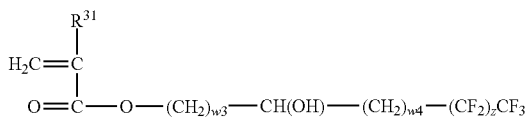 (5)

wherein $R^{31}$ represents a hydrogen atom, a methyl group, an ethyl group, or a propyl group; w3 and w4 each independently represent an integer of 1 to 6; and z represents an integer of 1 to 6,

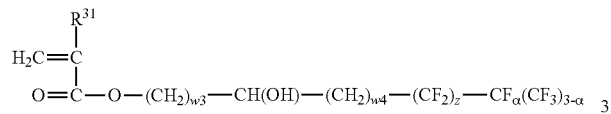 (6)

wherein $R^{31}$ represents a hydrogen atom, a methyl group, an ethyl group, or a propyl group; w3 and w4 each independently represent an integer of 1 to 6; z represents an integer of 1 to 6; and α represents an integer of 1 or 2.

13. The surface modification method according to claim 9, wherein the fluoro group is a fluoroalkylene oxide group or a fluorobenzyl group.

14. The surface modification method according to claim 9, wherein the fluoro group-containing monomers are at least one selected from the group consisting of
[1H,1H-perfluoro(2,5-dimethyl-3,6-dioxanonanoyl)] acrylate,
[1H,1H-perfluoro(2,5-dimethyl-3,6-dioxanonanoyl)] methacrylate,
pentafluorobenzyl acrylate,
pentafluorobenzyl methacrylate, and
2,3,5,6-tetrafluorophenyl methacrylate.

15. The surface modification method according to claim 1, wherein the (liquid) radical polymerizable monomers or a solution thereof contains a polymerization inhibitor, and the monomers are polymerized in the presence of the polymerization inhibitor.

16. The surface modification method according to claim 15, wherein the polymerization inhibitor is 4-methylphenol.

17. The surface modification method according to claim 1, wherein the polymer chains are 10 to 50000 nm in length.

18. A surface-modified elastic body, which is obtained by the surface modification method according to claim 1.

19. A surface-modified elastic body, which needs to have sliding properties, low friction, or low water resistance in the presence of water or in a dry state, and which is obtained by the surface modification method according to claim 1.

20. A surface-modified elastic body, which is a three-dimensional solid having at least partially a surface modified by the surface modification method according to claim 1.

21. The surface-modified elastic body according to claim 18, which is a polymer brush.

22. A gasket for syringes, which has at least partially a surface modified by the surface modification method according to claim 1.

23. A catheter, which has at least partially a surface modified by the surface modification method according to claim 1.

24. A tire, which has at least partially a groove surface modified by the surface modification method according to claim 1.

25. A tire, which comprises a sidewall having at least partially a surface modified by the surface modification method according to claim 1.

26. A surface modification method for modifying a rubber vulcanizate or a thermoplastic elastomer as an object to be modified, the method comprising:
Step 1 of allowing a photopolymerization initiator to be adsorbed on a surface of the object to be modified; and
Step 2 of radical polymerizing zwitterionic monomers and/or fluoro group-containing monomers, starting from the adsorbed photopolymerization initiator, by irradiation with UV light at a wavelength of 300 nm to 400 nm to grow polymer chains on the surface of the object to be modified.

* * * * *